United States Patent [19]

Allenza

[11] Patent Number: 5,049,494
[45] Date of Patent: Sep. 17, 1991

[54] CONVERSION OF MANNOSE TO FRUCTOSE

[75] Inventor: Paul Allenza, Flemington, N.J.

[73] Assignee: Allied-Signal Inc., Morris Township, Morris County, N.J.

[21] Appl. No.: 307,450

[22] Filed: Feb. 8, 1989

[51] Int. Cl.$^5$ ............ C12P 19/02; C12N 11/00; C12N 9/90; C12N 1/20

[52] U.S. Cl. ............ 435/105; 435/874; 435/233; 435/253.3; 435/174; 435/176; 435/177; 435/181; 435/182

[58] Field of Search ............ 435/105, 874, 233, 253.3, 435/174, 176, 177, 181, 182

[56] References Cited

U.S. PATENT DOCUMENTS 4,141,857 2/1979 Levy et al. ............ 252/430
4,492,755 1/1985 Horwath ............ 435/94

OTHER PUBLICATIONS

Palleroni and Doudoroff, *J. Biol. Chem.*, 218, 535 (1956).
Takasaki, *Agr. Biol. Chem.*, 31, 435 (1967).
Hey-Ferguson and Elbein, *J. Bacteriology*, 101, 777 (1970).
Mayo et al., *Carbohyd. Res.*, 8, 344 (1968).
P. Allenza, PhD. Dissertation, Feb., 1983, Univ. of Mass., pp. 69 to 75.
Herrick et al., Applied Polymer Symposium, No. 28, 93–108 (1975).
J. H. Roe, *J. Biol. Chem.*, 107: 15–19 (1934).

*Primary Examiner*—Johnnie R. Brown
*Assistant Examiner*—Pamela S. Webber
*Attorney, Agent, or Firm*—Eugene I. Snyder; Harold N. Wells; Gerhard H. Fuchs

[57] ABSTRACT

An economical method of converting mannose to fructose uses a mannose isomerase from *Pseudomonas cepacia* immobilized on an alumina containing polyethyleneimine crosslinked with an excess of glutaraldehyde. The method utilizes mannose-containing aqueous solutions as the feedstock, and affords solutions in which at least 55% of the mannose has been converted to fructose. Because of the relatively higher levels of fructose than can be obtained by isomerizing glucose to fructose using glucose isomerase, substantial savings in separation of high fructose-containing products can be achieved. The process described represents the first economical mannose isomerase process.

7 Claims, 3 Drawing Sheets

Rate Of Conversion Of Mannose To Fructose.

Rate Of Conversion Of Mannose To Fructose.

CONVERSION OF MANNOSE TO FRUCTOSE

BACKGROUND OF THE INVENTION

High fructose corn syrup (HCFS) is a widely used alternative to sucrose as a sweetener in many foods, and especially in soft drinks. High fructose corn syrup ultimately arises from the corn wet milling industry where starch is hydrolyzed, generally in a 2-stage process, to afford a starch hydrolyzate containing at least about 94% glucose, and the glucose is subsequently enzymatically isomerized to fructose using glucose isomerase (GI). Many variants of this process are known and have been successfully practiced for years.

The product of enzymatic isomerization of glucose is limited by equilibrium to about 50% fructose, whereas a high fructose corn syrup product approximately equal in sweetness to sucrose contains about 55% fructose. To attain the latter level commercially a portion of the product stream from enzymatic isomerization of glucose is sent to a separation unit, such as a chromatographic separation unit, to afford fractions containing about 90% fructose. These fructose-enriched fractions then are blended with the product stream to give the high fructose corn syrup of commerce.

Purified fructose, i.e., preparations containing at least 90% fructose, is a rather expensive commodity because the aforementioned separation process adds a substantial cost, especially when using a feedstock which is only about one-half fructose. Clearly there is an impetus for the production of fructose at levels greater than 50%, yet its equilibrium value from the isomerization of glucose cannot be significantly changed in a commercially practical matter. A 50% fructose content can be considered as a limitation inherent in the present method of HCFS production.

Several workers have reported that a microbial enzyme, mannose isomerase (MI), converts mannose to fructose with the equilibrium mixture containing about 70% fructose, which represents a substantial enrichment of fructose relative to the "glucose isomerase process" described above. Development of a "mannose isomerase process" alternative to fructose has been ignored, perhaps in part, because of the relative overabundance of corn and corn starch. But at least in principle a mannose isomerase process to fructose represents an option which circumvents the inherent limitations of a GI process.

However clear may be the principles involved, several problems need to be solved for an MI alternative to become commercially attractive. The microorganism producing mannose isomerase must grow rapidly in simple media and produce enzyme at a high level. The mannose isomerase must be able to be immobilized efficiently. The immobilized mannose isomerase should be quite specific as to substrate acted upon, should not need cofactors or be sensitive to inhibitors, and should have a reasonably long half-life under operating conditions. Finally, for a MI alternative process to be at all competitive it must be able to use a cheap, abundant feedstock which is geographically widely available.

Palleroni and Doudoroff [*J. Biol. Chem.*, 218, 535 (1956)] appear to have first discovered a mannose isomerase from mutant strains of *Pseudomonas saccharophila* grown on fructose as a substrate, and reported that the equilibrium mixture contained 71% fructose. Although the enzyme did not require any cofactors, the MI did act on some aldose substrates other than mannose. Somewhat later, Takasaki [*Agr. Biol. Chem.*, 31, 435 (1967)] reported that the mannose isomerase from *Streptomyces aerocolorigenes* isomerized mannose to afford 72–75% fructose at equilibrium, with the equilibrium constant being invariant with temperature over the range 1°–40° C. Hey-Ferguson and Elbein reported in *J. Bacteriology*, 101, 777 (1970) that the mannose isomerase from *Mycobacterium smegmatis* when grown on mannose isomerized the latter to afford 65% fructose at a pH optimum of 7.5. These investigators also reported the MI was active toward D-lyxnose. More recently, the patentees of U.S. Pat. No. 4,492,755 expanded on the prior work of Mayo et al. [*Carbohyd. Res.*, 8, 344 (1968)] by using mutants of *Klebsiella aerogenes* as well as species from the genera *Escherichia* and *Lactobacillus* which were constitutive MI producers to isomerize L-mannose to L-fructose. According to examples of the patentee the isomerization appears to require Co(II) ions during the isomerization.

Allenza reported that *Pseudomonas cepacia* produces a mannose isomerase intracellularly [P. Allenza, Ph.D. Dissertation, February, 1983, Univ. of Massachusetts, pp 69 to 75]. This microorganism was found to multiply rapidly on simple growth media under ordinary conditions to produce reasonably high levels of the enzyme, thus meeting two of the aforementioned criteria for an MI process. I have subsequently discovered that the mannose isomerase can be immobilized from unpurified whole cell extracts with high efficiency and without interference from other enzymes and without diminution of MI activity. The immobilized MI as prepared from unpurified whole cell extracts exhibits quite specific enzymatic activity and functions effectively either on solutions of purified mannose or, under appropriate circumstances, on a mannose containing feedstock widely available from the wood pulping industry and otherwise viewed as an industrial waste. Although mannose may constitute only about 40% of the dry solids of the latter feedstock, the high selectivity of the immobilized mannose isomerase as prepared from unpurified whole cell extracts described within effects the conversion of mannose to fructose without other detectable reactions. The immobilized MI needs no cofactors and does not appear to be inhibited by materials found or likely to be found in the feedstocks described above, and functions well in the absence of cobalt ions. Finally, the immobilized mannose isomerase as described within is sufficiently stable at operating conditions to be used over acceptable periods of time without change. In summary, I have appreciably enlarged the scope of knowledge pertinent to a mannose isomerase process alternative and have specified in detail means for economically producing fructose from cheap, abundant, and widely available feedstocks. My invention utilizes the inexpensive but highly efficient immobilization of crude mannose isomerase, an inexpensive source of mannose isomerase, and an inexpensive feedstock leading to the less expensive isolation of purified fructose. In its totality our invention provides the first economical mannose isomerase process alternative.

SUMMARY OF THE INVENTION

The purpose of this invention is to convert at least 55% mannose in a cheap, readily available feedstock to fructose in a continuous manner using an immobilized mannose isomerase, and to perform this conversion cheaply and efficiently. In an embodiment a mannose-containing feedstock is isomerized with a mannose isomerase immobilized on a support of a refractory inorganic oxide impregnated with a polyamine which has been crosslinked with an excess of a bifunctional reagent so as to furnish pendant functional groups. In a more specific embodiment the enzyme is that from *Pseudomonas cepacia*. In a still more specific embodiment the enzymatic isomerization is conducted at a pH between about 5 and about 8.5. Other embodiments and purposes will be clear from the ensuing description.

DESCRIPTION OF THE INVENTION

Figure 1:
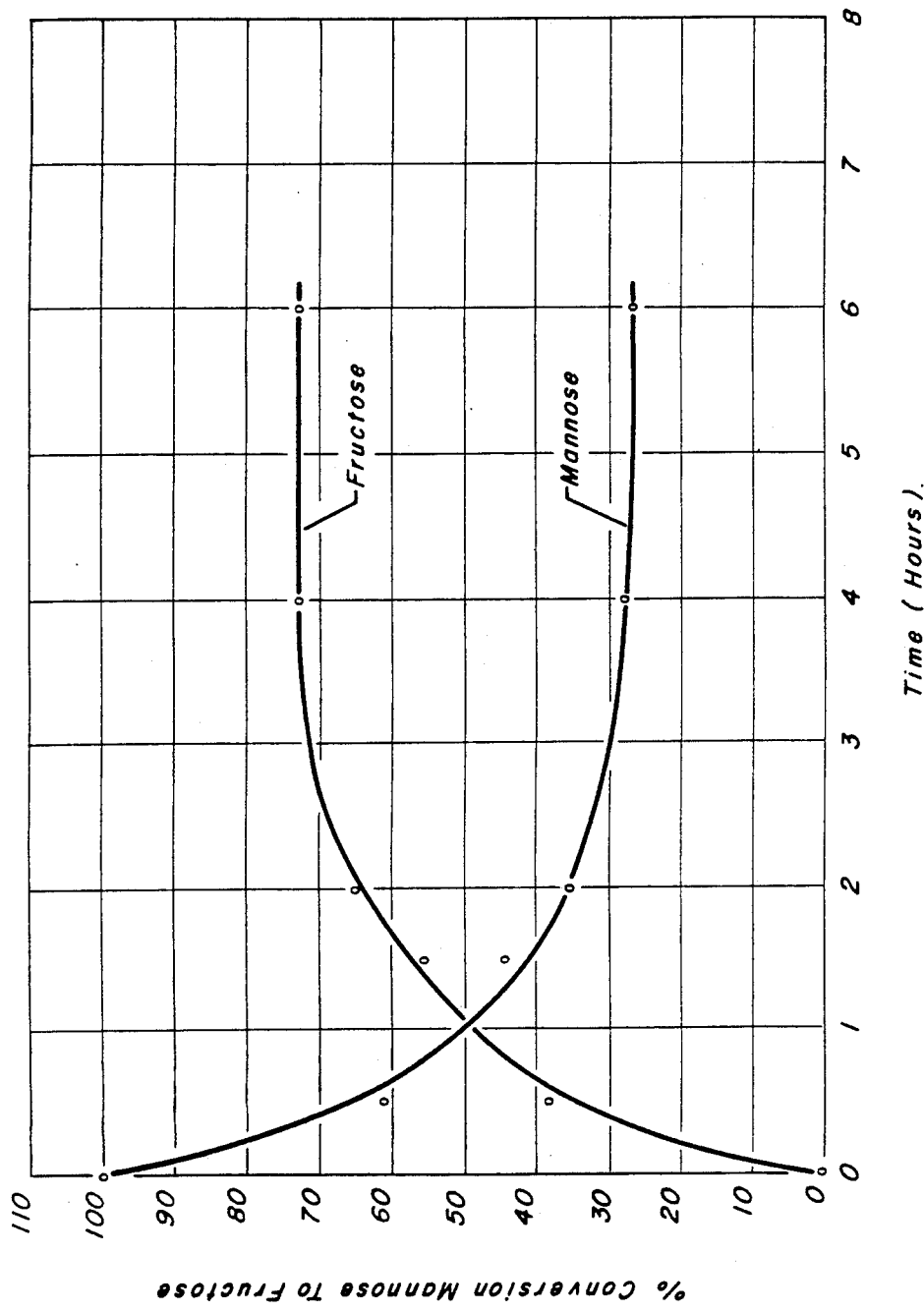
FIG. 1 shows a typical approach to equilibrium in isomerization of mannose to fructose using immobilized mannose isomerase.

This invention is an economical method of preparing fructose from a cheap, readily available source of mannose in a continuous process. The invention results from the use of an immobilized mannose isomerase where the enzyme is produced from a microorganism with fast growth in a simple medium with high production of mannose isomerase. The mannose isomerase is intracellular, yet stable as an immobilized enzyme at operating conditions. The isomerase is very specific, requires no cofactors or salts, and is readily immobilized from a crude enzyme preparation. The result is a process which is the first enabling production of fructose from a widely available source of mannose both efficiently and quite economically.

A central feature of my invention is the isomerization of mannose to fructose. Where the object is to prepare and isolate purified fructose, the separation process employed often is most cost effective when the mixture to be separated contains only two components (fructose and mannose) at as high a level of dry solids consistent with other operational considerations. In these circumstances a preferred feedstock for isomerization by immobilized mannose isomerase is a solution of purified mannose containing from about 5 to about 50 weight percent dry solids. Spent liquors generated by conifer wood-pulping processes are rich in mannose, and isolation of mannose from the liquors via the bisulfite adduct, inter alia, has been described by Herrick et. al., *Applied Polymer Symposium*, No. 28, 93–108 (1975).

Although a feedstock of a solution of purified mannose will afford the simplest product mixture after enzymatic isomerization by mannose isomerase, it is not necessarily the only feedstock which can be used. Where fructose can be very easily separated from other monosaccharides and from disaccharides, or where only mixtures containing a relatively high proportion of fructose is acceptable, then a delignified hemicellulose hydrolyzate may be used as the feedstock. Hemicellulose, particularly hemicelluloses from softwoods, are rich in mannose as a component in the complex polymeric structures. However, hemicelluloses are readily hydrolyzable to afford complex mannose-containing aqueous solutions. Hemicellulosic wood wastes include the non-cellulosic carbohydrates extracted from coniferous wood chips during their conversion into high grade wood pulps and hardboards, and the cold alkaline extract material removed from wood pulps during the refining and bleaching stages. These are merely exemplary of the mannose-containing aqueous hemicellulose hydrolysates from wood wastes which, in appropriate cases, may be used as the feedstock in the practice of my invention and which are found in large quantities throughout the world.

It is emphasized again that the choice of mannose-containing feedstock may depend upon the overall purpose of the process. Where the purpose is to isolate purified fructose per se a purified mannose solution may be the most desirable feedstock. However, if the separation process for fructose is highly discriminatory, or where one only seeks a mixture of monosaccharides containing a relatively high proportion of fructose, other mannose-containing feedstocks may be usable. The mannose-containing hemicellulose hydrolysates may have a dry solids level in the range from about 5 to about 50%, although the dry solids content of the feedstocks used in the practice of this invention is not an important feature. Such feedstocks may contain as little as about 2–3% mannose, although it should be apparent that the higher the mannose level the more desirable is the feedstock at the same feedstock price. More typically the feedstocks will contain from about 10 to about 45 weight percent mannose on a dry solids basis.

The mannose-containing aqueous feedstock is enzymatically isomerized with an immobilized mannose isomerase. The support used for the immobilization of the enzyme is that described in U.S. Pat. No. 4,141,857. This support is a refractory inorganic oxide which is coated with a polyamine which has been crosslinked with an excess of a bifunctional reagent so as to afford a multiplicity of pendant functional groups. The refractory inorganic oxide used generally is selected from the group consisting of alumina, silica, thoria, titania, magnesia, and combinations thereof, with alumina being a particularly preferred refractory inorganic oxide. Among the polyamines which are used are included diethylenetriamine, triethylenetetraamine, tetraethylenepentaamine, pentaethylenehexamine, and polyethyleneimine, with polyethyleneimine being most desired. After the inorganic oxide is impregnated with the polyamine, the latter is crosslinked by an excess of the polyfunctional reagent which is selected from the group consisting of phthalaldehyde, toluene diisocyanate, and compounds of the formula $X(CH_2)_pX$, where p is an integer from 2 to about 8 and X is —NCO or —CHO so as to afford a multiplicity of pendant functional groups. The class of dialdehydes, X=—CHO are the preferred polyfunctional reagents, and glutaraldehyde is an especially favored crosslinking agent.

To be used in the practice of my invention, the mannose isomerase should have the characteristics of requiring no cofactors, requiring no salts for its activity, exhibiting high selectivity toward mannose vis-a-vis other monosaccharides which may be found in the feedstock, and exhibiting little inhibition by materials likely to be found in the feedstock. A preferred source of enzyme is the microorganism *Pseudomonas cepacia* which has been described in P. Allenza, Ph.D. Dissertation, February, 1983, Univ. of Massachusetts, pp. 69 to 75.

A particularly desirable feature of the mannose isomerase produced by *P. cepacia* is that essentially all of its isomerase activity is immobilized from an impure enzyme extract without immobilization of interfering enzymes, such as those which destroy fructose. Thus, the immobilized mannose isomerase may be readily prepared merely by rupturing the cell walls to release the intracellular enzyme, removing the cell debris, and using the crude enzyme extract from which to immobilize the mannose isomerase.

Although intracellular enzymes often are unstable, the mannose isomerase from P. cepacia shows good stability at operating temperatures. For example, the half-life of the immobilized enzyme at 40° C. is about 5 days. The immobilized enzyme also shows a very flat pH optimum in the range of 5 to 8.5, exhibiting about 80% of its activity at both ends of this range. The optimum isomerase activity of the immobilized enzyme occurs at a pH between about 7 and 7.5.

The mannose-containing feedstock is enzymatically isomerized with the immobilized mannose isomerase at a temperature between about 30° to about 60° C., the optimum temperature range being from about 35° to about 45° C. Isomerization typically is conducted by passing the aqueous feedstock through a bed of the immobilized mannose isomerase at a liquid hourly space velocity sufficient to give a resident time so as to convert at least about 55% of the mannose to fructose. Although the equilibrium value in the mannose-fructose conversion represents about 70–75% fructose, generally it is more economical to conduct the enzymatic conversion up to a point short of the equilibrium value for the sake of overall productivity. For example, it takes only about ⅓ as much time to produce a feedstock containing 55% fructose as that containing the equilibrium value of fructose. Similarly, conversion of about 60% mannose takes somewhat more than 40% as much time, and conversion of about 65% mannose takes only about 60% of the time required for complete equilibration. Thus, reaction typically will be conducted for a time to produce at least about 55% conversion of mannose. Where desired, the conversion can be run to at least 60 or 65% mannose, or even higher where desirable.

For the preparation of high fructose corn syrup, my invention can be utilized in several different ways. In one mode a mannose-containing feedstock is isomerized and the purified fructose which is recovered from the product mixture as by chromatographic or membrane separation, is blended into a fructose-glucose mixture from GI isomerization of glucose. This variant incorporates a minimum of foreign saccharides into HCFS.

Where larger amounts of foreign saccharides, especially mannose, can be tolerated in HCFS, a product mixture from the MI process can be purified to afford essentially mannose-fructose mixtures which are predominantly fructose. These fructose-enriched mannose-fructose mixtures then can be blended with fructose-glucose mixtures to afford a product of appropriate sweetness.

The following examples are merely illustrative of the practice of my invention and are not intended to limit it in any way.

EXAMPLES

For production of mannose isomerase, Pseudomonas cepacia was grown in an inorganic salts medium consisting of 50 mM phosphate buffer (16 mM $Na_2HPO_4$ and 34 mM $KH_2PO_4$), pH 6.5, 1 mM $MgSO_4$, 0.1 mM $CaCl_2$, 0.01 mM $FeSO_4$, and 0.2% wt/vol ammonium sulfate. One per cent D-mannose was used as the sole source of carbon, although 0.5% D-mannose could be used with only slightly lower enzyme yields. The bacteria were grown at 37° C. typically for 20 to 24 hours.

For preparation of an enzyme extract, cells were collected from the fermentation broth by centrifugation, washed in 20 mM phosphate buffer, pH 6.8, recentrifuged, and then suspended in a volume of buffer equivalent to about 1/100th of the original fermentation volume. The washed cells were sonicated and unbroken cells and cell debris were removed by centrifugation. The resulting crude enzyme extract could be used for immobilization but it was found preferable to remove nucleic acids by precipitation, as by using streptomycin sulfate. In a typical example 1500 ml fermentation broth produced a cell extract of 28 ml containing 2433 units of mannose isomerase per ml. The resulting supernatant after nucleic acid removal was 35 ml with 2222 units/ml. It was found that recovery of enzyme following sonication and nucleic acid precipitation could be increased by 30% if the streptomycin sulfate (0.125 g/ml extract) was added to the crude extract prior to the centrifugation to remove cell debris.

For immobilization of mannose isomerase, 13.1 ml of the resulting extract (pH 6.6) was added to approximately 3.0 grams (2.6 ml) of a support which was alumina impregnated with polyethyleneimine crosslinked with an excess of glutaraldehyde. The enzyme was incubated with the support at 4° C. with intermittent shaking. Enzyme loading onto the support was estimated by measuring enzyme loss from the supernatant fluid using standard assay procedures as described below. Estimates made in this manner were compared to the activity of an enzyme preparation stored under the same conditions without the support in order to discount loss due to inactivation. After 18 hours 88.5% of the enzyme was immobilized onto the support, and after 42 hours 94.7% was immobilized. The support was then packed into a fixed bed reactor and connected to a peristaltic pump for feed delivery. The reactor was maintained at 4° C. overnight during which time the immobilized enzyme was flushed with over 200 bed volumes of 100 mM Tris buffer, pH 6.8, to remove any free or weakly bound enzyme. Washing of the immobilized enzyme in this manner did not result in loss of immobilized enzyme activity i.e., the enzyme was stably immobilized. The immobilized enzyme was subsequently flushed with the mannose substrate for several hours prior to assay.

Mannose isomerase activity was typically determined at 40° C. using a feedstock containing 0.1M D-mannose and 0.2M Tris buffer at pH 6.5. Mannose isomerase activity was determined in extracts primarily by measuring mannose-dependent formation of fructose according to the method described by J. H. Roe, J Biol. Chem. 107: 15–19 (1934). Assay mixtures (1 ml) containing 200 mM Tris buffer, pH 7, 100 mM D-mannose, and appropriately diluted cell extract were incubated at 40° C. After 15 min., 0.2 ml of each reaction mixture was transferred to a separate tube and 0.2 ml of ethanol containing 0.1% (wt/vol) resorcinol and 0.6 ml of 10N HCl was added. The tubes were incubated at 80° C. for 8 min, and then placed in ice water to stop the reaction. The absorbance at 484 nm was determined and compared to a standard curve relating absorbance to fructose concentration. An absorbance of 0.1 was equivalent to 150 nmoles of fructose per ml of assay mixture. The conversion of mannose to fructose (as well as any reactions with other sugars) was also determined using HPLC and known standards. A typical conversion of mannose to 73% fructose and 27% mannose is shown in FIG. 1.

Figure 2:
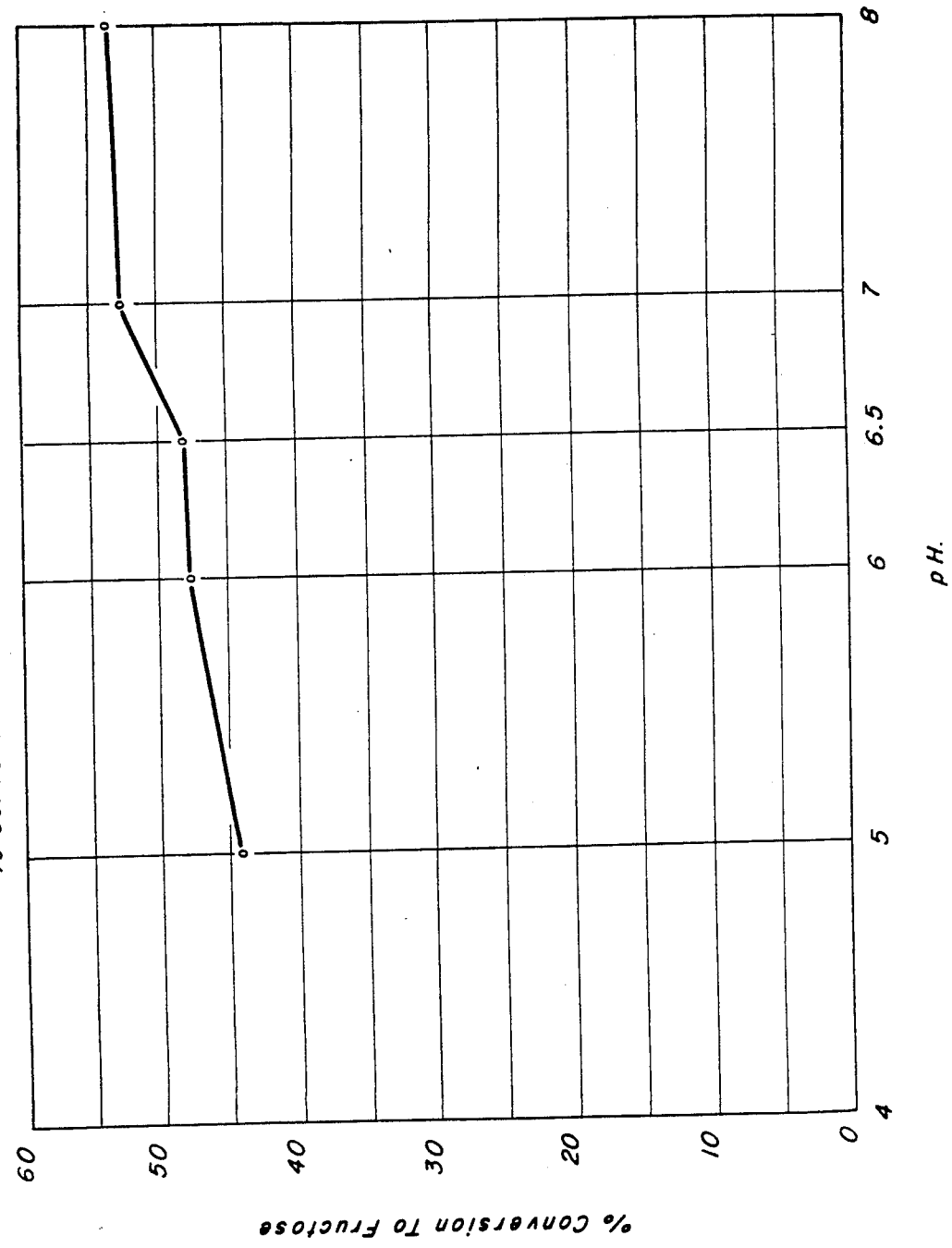
FIG. 2 shows the pH dependence of immobilized mannose isomerase activity.
Figure 3:
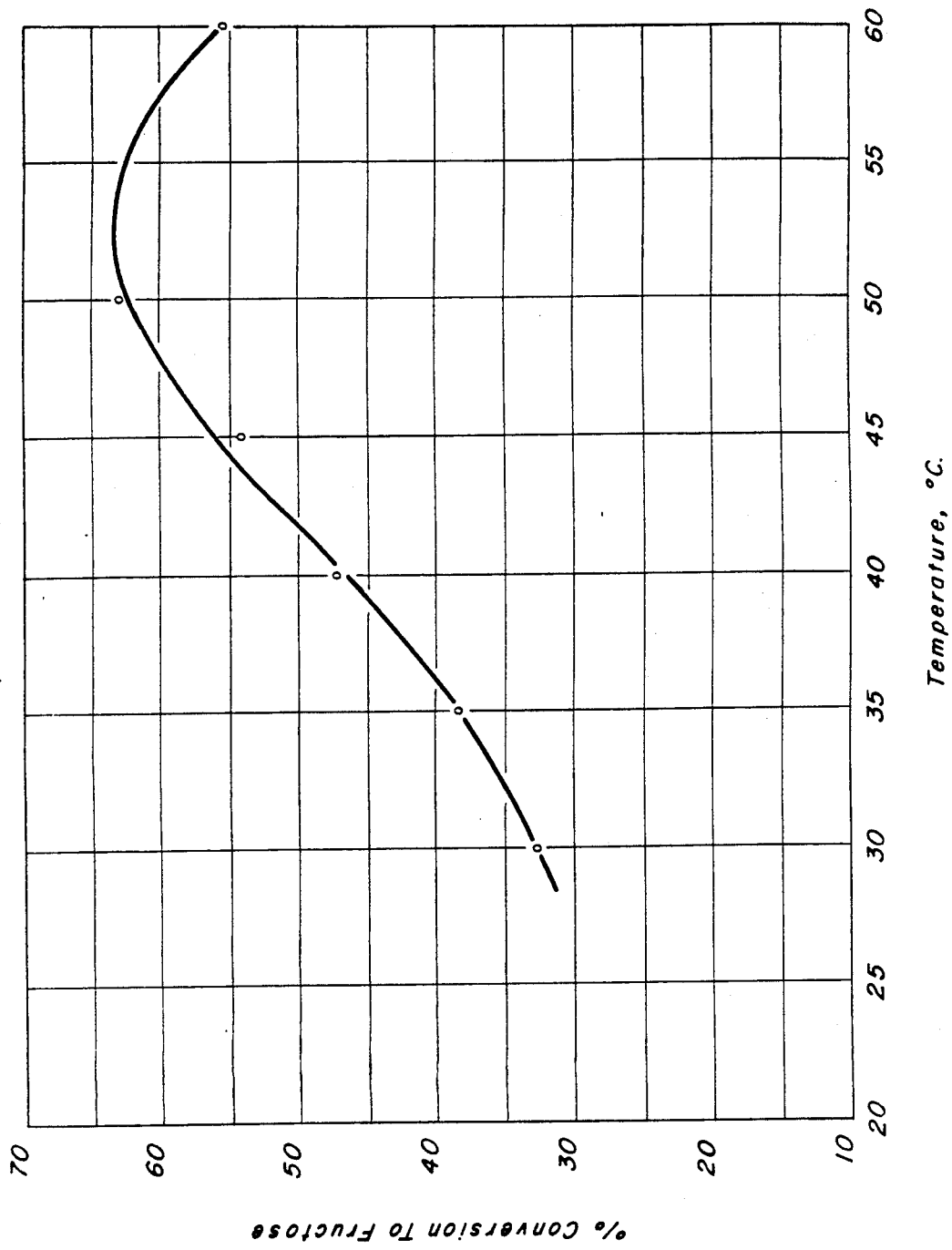
FIG. 3 shows the temperature dependence of immobilized mannose isomerase activity.

To determine the pH optimum of the immobilized enzyme the percent conversion of mannose to fructose was determined after a set period of time with the reactor in a batch recycle mode of operation. Before each test of the immobilized enzyme the reactor was operated under standard conditions of pH 7 at 40° C. to test for any inactivation. With each change of an operating variable the immobilized enzyme was allowed to equilibrate by passing a minimum of 50 bed volumes of feed through the column before the product concentrations were measured. The results (FIG. 2) showed a broad pH optimum with 90% of maximal activity between pH 6 and 8. In a similar manner the activity of the immobilized mannose isomerase was determined between 30° C. and 60° C. The results after one hour of operation in a batch recycle mode are shown in FIG. 3.

A similar set of experiments was used to test the behavior of the enzyme in the presence of other sugar substrates. For such experiments a mixed sugar feed was prepared approximating the ratios of hemicellulose-derived sugars identified in sulfite waste liquor streams and containing (in grams per liter of 0.2M Tris buffer at pH 7) galactose (15.9), glucose (15.9), mannose (40.3), arabinose (8.0), and xylose (15.2),. Under these conditions the immobilized enzyme maintained a rate of 55% of the rate of conversion under optimal conditions with mannose as the sole substrate. No new products other than fructose (derived from mannose) were identified using HPLC. The specificity of the immobilized enzyme was confirmed by removing small aliquots of the immobilized enzyme (0.4 g) and incubating them at 40° C. in 5 ml of 0.1M solutions of the following sugar solutions: D-galactose, L-arabinose, L-rhamnose, D-xylose, D-lyxose, D-xylulose, L-mannose and D-mannose (control). After 18 hours, there was a 68% loss of D-mannose (due to conversion to D-fructose) but no detectable loss of other sugars.

What is claimed is:

1. A method for producing fructose comprising enzymatic isomerization of mannose in an mannose-containing aqueous feedstock comprising a delignited hemicellulose hyrolysate with a mannose isomerase immobilized on a support, said isomerization conducted at a temperature from about 30° to about 60° C. and a pH from about 5 to about 8.5 for a time sufficient to convert at least 55% of the mannose to fructose, and recovering the isomerized product mixture, where said mannose isomerase has the characteristics of the mannose isomerase produced by pseudomonas cepacia and said support comprises a refractory inorganic oxide selected from the group consisting of alumina, silica, thoria, magnesia, titania, and combinations thereof, impregnated with a polyamine selected from the group consisting of ethylenediamine, diethylenetriamine, triethylenetetraamine, tetraethylenepentaamine, pentaethylenehexaamine, and polyethyleneimines, said polyamine being crosslinked with an excess of a bifunctional reagent selected from the group consisting of phthalaldehyde, toluene diisocyanate, and $X(CH_2)_pX$, where p is an integer from 2 to about 8 and $X=-CN$ or $-CHO$, so as to provide a multiplicity of pendant functional groups.

2. The method of claim 1 where the aqueous mannose-containing feedstock comprises an aqueous solution of purified mannose.

3. The method of claim 1 where the mannose isomerase is immobilized on a support of alumina impregnated with a polyethyleneimine crosslinked with an excess of glutaraldehyde so as to afford a multiplicity of pendant aldehyde groups.

4. The method of claim 1 where the isomerization is performed at a temperature between about 35° to about 45° C.

5. The method of claim 1 where the isomerization is conducted at a pH between about 7 and about 7.5.

6. The method of claim 1 where the isomerization is conducted for a time sufficient to convert at least 60% of the mannose to fructose.

7. The method of claim 1 where the isomerization is conducted for a time sufficient to convert at least 65% of the mannose to fructose.

* * * * *